United States Patent
Fotheringham et al.

(10) Patent No.: US 11,400,173 B2
(45) Date of Patent: Aug. 2, 2022

(54) SANITIZING BOTTLE

(71) Applicant: LUMA HYDRATION INC., Orem, UT (US)

(72) Inventors: Brett Fotheringham, Arlington, TX (US); August Simmons, Arlington, TX (US); Jacob Starley, Arlington, TX (US); Aaron Janke, Arlington, TX (US); William Hogan, Arlington, TX (US)

(73) Assignee: LUMA HYDRATION INC., Orem, UT (US)

( * ) Notice: Subject to any disclaimer, the term of this patent is extended or adjusted under 35 U.S.C. 154(b) by 357 days.

(21) Appl. No.: 16/252,678

(22) Filed: Jan. 20, 2019

(65) Prior Publication Data
US 2020/0230269 A1    Jul. 23, 2020

(51) Int. Cl.
| | | |
|---|---|---|
| *A61L 2/10* | (2006.01) | |
| *C02F 1/32* | (2006.01) | |
| *B65D 51/24* | (2006.01) | |
| *B65D 53/02* | (2006.01) | |
| *B65D 1/02* | (2006.01) | |
| *A61L 2/24* | (2006.01) | |

(52) U.S. Cl.
CPC ............... *A61L 2/10* (2013.01); *A61L 2/24* (2013.01); *B65D 1/02* (2013.01); *B65D 51/242* (2013.01); *B65D 53/02* (2013.01); *C02F 1/325* (2013.01); *A61L 2202/11* (2013.01); *A61L 2202/14* (2013.01); *A61L 2202/16* (2013.01); *A61L 2202/23* (2013.01); *C02F 2201/3222* (2013.01)

(58) Field of Classification Search
CPC .......... A61L 2/10; A61L 2/24; A61L 2202/11; A61L 2202/14; B65D 1/02; B65D 53/02; B65D 51/242; C02F 1/325
See application file for complete search history.

(56) References Cited

U.S. PATENT DOCUMENTS

| | | | |
|---|---|---|---|
| 6,579,495 B1 | 6/2003 | Maiden | |
| 7,390,417 B2 | 6/2008 | Kuhlmann et al. | |
| 8,203,124 B2 | 6/2012 | Havens et al. | |
| 8,282,880 B2 | 10/2012 | James | |
| 8,816,300 B1 * | 8/2014 | Walker | C02F 1/325 250/453.11 |
| 8,872,130 B1 | 10/2014 | Matthews et al. | |
| 10,738,446 B1 * | 8/2020 | Munn | A61L 2/24 |

(Continued)

FOREIGN PATENT DOCUMENTS

WO    2016189800 A1    12/2016
WO    WO 2018/187681 A1 *    10/2018

*Primary Examiner* — Sean E Conley
(74) *Attorney, Agent, or Firm* — Workman Nydegger

(57) ABSTRACT

Systems, devices, and methods are disclosed herein for providing a sanitizing bottle. A sanitizing bottle includes a storage body to store liquid; a cap configured to removably attach to the storage body; a cap sensor disposed on the storage body to determine whether the cap is attached to the storage body; a UV emitter to emit UV light in the storage body; and a processor coupled to the cap sensor and the UV emitter. The processor is to activate the UV emitter responsive to determining, via the cap sensor, the cap is attached to the storage body. The processor is to deactivate the UV emitter responsive to determining, via the cap sensor, the cap is not attached to the storage body.

17 Claims, 3 Drawing Sheets

(56) References Cited

U.S. PATENT DOCUMENTS

| | | |
|---|---|---|
| 2011/0104017 A1 | 5/2011 | Migliore et al. |
| 2011/0226966 A1 | 9/2011 | Takahashi et al. |
| 2013/0319915 A1* | 12/2013 | Gellibolian ............. C02F 1/002 |
| | | 210/87 |
| 2016/0289090 A1 | 10/2016 | Liao et al. |
| 2017/0280737 A1* | 10/2017 | Liao ....................... C02F 1/725 |
| 2020/0146306 A1 | 5/2020 | Liao et al. |

* cited by examiner

SANITIZING BOTTLE

TECHNICAL FIELD

Aspects of the present disclosure relate to reusable bottles for storing liquid, and in particular to bottles having self-cleaning apparatuses.

BACKGROUND

Reusable bottles are manufactured in a variety of shapes and sizes to match the convenience of users with varying lifestyles. However, the vast majority of reusable bottles have one feature in common: they utilize a water-tight cap to keep liquid stored in the bottle from spilling. Conventional water-tight caps have undesirable limitations.

Bottles which are closed with a water-tight cap often produce a foul odor after prolonged use. Bacteria is often introduced into a reusable bottle by means of impurities within the liquid stored in the bottle or by the user of a bottle who places their lips onto the bottle's outlet. When a bottle is sealed, the flow of oxygen into the liquid and the bottle itself is cut off, causing the growth of bacteria. These bacteria produce an undesirable odor, and bottle users must routinely clean their bottles to avoid having to drink from an odorous bottle. Some people choose to avoid reusable bottles altogether in order to avoid this inconvenience, electing instead to use disposable bottles which are less environmentally sustainable.

SUMMARY

The following is a simplified summary of the disclosure in order to provide a basic understanding of some aspects of the disclosure. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

In an aspect of the disclosure, a sanitizing bottle includes a storage body to store liquid; a cap configured to removably attach to the storage body; a cap sensor disposed on the storage body to determine whether the cap is attached to the storage body; a UV emitter to emit UV light in the storage body; and a processor coupled to the cap sensor and the UV emitter. The processor is to activate the UV emitter responsive to determining, via the cap sensor, the cap is attached to the storage body. The processor is to deactivate the UV emitter responsive to determining, via the cap sensor, the cap is not attached to the storage body.

BRIEF DESCRIPTION OF THE DRAWINGS

In order that the advantages of the present disclosure will be readily understood, a more particular description of the present disclosure briefly described above will be rendered by reference to specific embodiments illustrated in the appended drawings. Understanding that these drawings depict only typical embodiments of the present disclosure and are not therefore to be considered limiting of its scope, the present disclosure will be described and explained with additional specificity and detail through use of the accompanying drawings, in which.

DETAILED DESCRIPTION

Figure 1A:
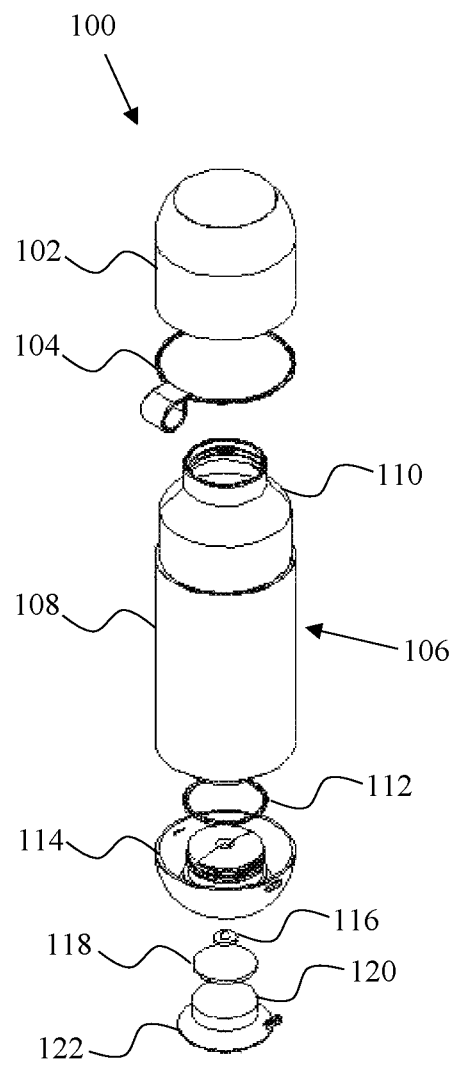
FIG. 1A shows an exploded view of a self-sanitizing bottle, according to certain embodiments.

Described herein are technologies related to sanitizing bottles. Conventional bottles with a water-tight cap produce a foul odor due to bacteria growth (e.g., responsive to cutting off flow of oxygen). The foul odor of conventional bottles with a water-tight cap may cause users to frequently clean or to discard the bottles.

The devices, systems, and methods disclosed herein provide sanitizing bottles (e.g., reusable sanitizing bottles). A sanitizing bottle may include a cap, storage body, and base assembly. The cap is configured to be removably attached to the storage body. A sensor may be disposed on the storage body and may be coupled to a processor in the base assembly for detecting whether the cap is in an attached or detached configuration. A storage body may have a liquid inlet portion that forms an upper opening and an ultraviolet (UV) light inlet portion forming a lower opening. The liquid inlet portion may be configured to contact and attach to the cap and allow the passage of liquid in and out of the storage body. The UV light inlet portion may be configured to attach to the base assembly and allow the passage of UV light emitted from an emitter in the base assembly. A reflective interior surface of the storage body may enable more efficient use of power provided by a battery in the base assembly by decreasing the length of time required for a sanitizing operation to kill bacteria within a stored liquid and on the interior surface of the storage body.

The base assembly includes the battery, UV emitter, processor, and a timer, each configured to allow the processor to execute a sanitizing operation. A switch assembly is disclosed which allows a user to manually initiate a sanitizing operation in some embodiments. The sanitizing operation is terminated on completion of a predetermined time delay known to kill a sufficient percentage of bacteria within a bottle or upon detection of removal of the cap from the storage body. In some embodiments, a predetermined time delay of 60 seconds is sufficient for a sanitizing operation to kill 99.99% of bacteria within the sanitizing bottle. In some embodiments, the predetermined time delay may be between 30 and 90 seconds for a sanitizing operation to kill 99% of bacteria within the sanitizing bottle. The sanitizing bottle may include LED lights which are operable by the processor and indicate the status of a sanitizing operation of the bottle in some embodiments.

Aspects of the disclosure result in advantages such as preventing bacteria growth in a reusable bottle (e.g., prevent the growth of odor-producing bacteria). The sanitizing bottle, as described herein, may be as portable as conventional reusable bottles, and may require less maintenance or inconvenience to a user to maintain in a usable, odor-free state compared to conventional bottles.

The present disclosure has been developed in response to the present state of the art and, in particular, in response to the problems and needs in the art that have not yet been fully solved by currently available systems. Accordingly, a sanitizing bottle has been developed. Features and advantages of different embodiments of the present disclosure will become more fully apparent from the following description and appended claims or may be learned by practice of the present disclosure as set forth hereinafter.

It will be readily understood that the components of the present disclosure, as generally described and illustrated in the Figures herein, could be arranged and designed in a wide variety of different configurations. Thus, the following more detailed description of the embodiments of the present disclosure, as represented in the Figures, is not intended to limit the scope of the present disclosure, as claimed, but is merely representative of certain examples of presently contemplated embodiments in accordance with the present disclosure. The presently described embodiments may be understood by reference to the drawings, wherein like parts are designated by like numerals throughout.

Referring to FIG. 1A, an exploded view of an embodiment of a bottle 100 is shown, according to certain embodiments. The bottle 100 includes a cap 102 removably attachable to a storage body 106. The cap 102 may be attached to the storage body 106 by a variety of configurations. In some embodiments, the cap 102 may be attached to the storage body 106 via threads (e.g., threaded surface) within the cap 102 which correspond to threads (e.g., threaded surface) on or within the storage body 106, such that a user may remove or attach the cap 102 by twisting it onto or off of the storage body 106 in alternate directions. In some embodiments, the cap 102 may be attached to the storage body 106 via one or more latches or by a pressure fit between the cap 102 and the storage body 106. The cap 102 forms a water-tight seal when attached to the storage body 106. In some embodiments the cap 102 includes an O-ring that presses against the opening 110 of the storage body 106 in order to form a water-tight seal when the cap 102 is in a closed configuration. In some embodiments the cap 102 includes sealing elements other than an O-ring (e.g., a circular seal, a compressible surface, etc.).

In the depicted embodiment, an attachment ring 104 is provided between the cap 102 and the storage body 106. The attachment ring 104 may be permanently affixed to the storage body 106 or removable to cater to the preferences of a user. In either configuration, the bottle 100 can be held by a user or secured to another object (e.g., when the cap 102 is in a closed configuration via the attachment ring 104. The attachment ring 104 may, for example, be attached to a backpack or luggage loop using a carabiner or key-chain ring. In embodiments wherein the attachment ring 104 is permanently affixed to the storage body 106, the bottle 100 can be held by a user or secured to another object even when the cap 102 is not in a closed configuration.

The storage body 106 forms an opening 110 through which liquid may enter and exit the bottle 100. The storage body 106 further includes a storage wall 108 (e.g., an exterior surface of the storage body). The outer perimeter (e.g., diameter) of the opening 110 is smaller than the outer perimeter (e.g., diameter) of the storage wall 108. In some embodiments, the storage wall 108 is cylindrical in shape). In some embodiments, the storage wall 108 is a shape other than cylindrical (e.g., rectangular prism, triangular prism, etc.) The storage wall 108 provides structural integrity to the bottle 100 by defining and maintaining shape of the bottle 100. The storage wall 108 has an inner wall which interfaces with liquid poured into or being poured out of the bottle 100 and which may have additional properties as further defined hereafter. In some embodiments, the storage wall 108 also has an outer wall which enhances the aesthetic quality of the bottle 100 and provides a user with a surface by which they can hold and grip the bottle 100. In some embodiments, the storage wall 108 includes a tapered portion for a gradual decrease in outer perimeter (e.g., diameter) from the storage wall 108 to the opening 110.

The bottle 100 depicted in FIG. 1A also includes a base assembly positioned on the opposite end of the storage body 106 from the cap 102. The base assembly is configured to emit UV light towards the inner walls of the storage body 106 and the cap 102. In some embodiments, the base assembly includes a sealing ring 112, a base cap 114, a UV emitter 116, a circuit 118, a battery 120, and a switch assembly 122. The sealing ring 112 is configured to ensure that a water-tight seal forms between the storage body 106 and the base cap 114, thereby protecting the remaining components in the base assembly from being damaged by liquid which would otherwise leak from the storage body 106.

In some embodiments, the base cap 114 is permanently affixed to the storage body 106. Such a permanent attachment may be accomplished by the use of adhesives, rivets, locked screws, or a pressure fit. In some embodiments, the base cap 114 is removably attached to the storage body 106. For example, the base cap 114 may be attached to the storage body 106 via threads (e.g., threaded surface) within the base cap 114 which correspond to threads (e.g., threaded surface) on or within the storage body 106, such that a user may remove or attach the cap 102 by twisting it onto or off of the storage body 106 in alternate directions. In some embodiments, the base cap 114 may be attached to the storage body 106 via one or more latches or by a pressure fit between the base cap 114 and the storage body 106. In some embodiments, the base cap 114 is removably attached to the storage body 106 in the same manner as the cap 102 so that a user can more intuitively understand how to assemble and disassemble the bottle 100 to perform maintenance. In other embodiments, the cap 102 is removably attached but the base cap 114 is permanently attached to the storage body 106 during manufacture to reduce the likelihood of user error, user injury, and damage to the components within the base assembly, thereby increasing overall reliability of the bottle 100.

The base cap 114 may form an opening through which UV light is emitted. In such a configuration, the UV emitter 116 is attached to the base cap 114 with a water-tight seal so that the UV emitter contacts liquid stored in the bottle 100 but liquid does not contact the circuit 118 or battery 120. In some embodiments, the base cap 114 comprises a lens, which contacts liquid stored in the bottle 100 on one side and faces the UV emitter 116 on the other side. The lens is configured within the base cap 114 such that a water-tight seal prevents stored liquid from contacting the UV emitter 116, circuit 118, or battery 120. The lens is transparent and may be made of a polymer or glass. The lens allows UV light emitted from the UV emitter to contact inner surfaces of the storage body 106 and may allow UV light emitted from the UV emitter to contact the inner surfaces of the cap 102.

In some embodiments, the UV emitter 116 emits UV-C light. The UV-C light emitted from the UV emitter 116 may be of sufficient intensity to kill bacteria within substantially any portion of the interior of the storage body 106 or cap 102 when the cap 102 is in a closed configuration. More specifically, in embodiments where the UV emitter 116 emits UV-C light, light with wavelengths between 290 nanometers (nm) to 100 nm, are emitted into the interior of the storage body 106 and cap 102 during a sanitizing operation. To increase efficiency of a sanitizing operation, one or more reflective materials may be incorporated in the interior of one or more of the storage body 106 or the cap 102. For example, the interior surface of one or more of the storage body 106 or the cap 102 may be made of a metal that reflects UV light, such as coated or uncoated steel (e.g., coated or uncoated stainless steel), coated or uncoated aluminum, glass, or the like. By incorporating a reflective surface, the intensity of UV light emitted from the UV emitter 116 can remain higher over time than in a bottle with a non-reflective interior, leading to a decrease in battery drain and a decrease in sanitizing operation time. In some embodiments, the UV emitter 116 emits light with wavelengths between 320 nm to 290 nm (e.g., UV-B light). In some embodiments, the UV emitter 116 emits light with wavelengths between 400 nm to 320 nm (e.g., UV-A light).

The circuit 118 may include one or more electrical components for facilitating the execution of the sanitizing operation. For example, the circuit 118 may include a processor, timer, and memory in some embodiments. The processor, which is in electrical communication with the switch assembly 122, may engage a program saved in memory which activates the UV emitter 116 responsive to the processor receiving a signal from the switch assembly 122. The processor may then enable the timer, causing the processor to keep the UV emitter 116 activated until a preset time period expires. In some embodiments, for sanitization of the liquid and bottle interior, the sanitizing operation is between 30 and 90 seconds. The sanitizing operation may be carried out by this type of program utilizing the circuit's electrical components. In some embodiments, the circuit 118 is also in electrical communication with other peripherals, such as one or more additional buttons, switches, or sensors. In the embodiment depicted in FIG. 2 and explained hereafter, for example, the circuit is in electrical communication with a wire extending to the cap 102 so that the processor may detect when the cap 102 is or is not in a closed position. In some embodiments, the processor may activate peripherals such as LED lights during and after the sanitizing operation to indicate to a user the status of the sanitizing operation. For example, the processor may cause one or more LED lights to blink or be a certain color while the sanitizing operation is underway and the UV emitter 116 is activated, and then cause one or more LED lights to operate in a different manner or color to indicate to a user that the sanitizing operation is complete. The appearance of LED lights may be manipulated by the processor by changing the power state of each LED individually or collectively.

The circuit 118 and other electronic peripherals are powered by a battery 120. The battery 120 may be a rechargeable battery or a single use battery, and may comprise one or more cells. The rechargeable battery may be recharged via one or more of a surface, port, etc. In some embodiments, the rechargeable battery includes an inductive charging area so that the battery 120 may be charged wirelessly responsive to the bottle being placed on an inductive charging pad. In some embodiments, a female port (e.g., charging port) is included in the base cap 114 and is configured to receive the male port of a charging cable. The female port may support a standard connection such as a universal serial bus (USB) connection. In some embodiments the female port is a female Micro-USB or USB-C port to increase the bottle's compatibility with other commonly used charging cables.

In the embodiment depicted in FIG. 1A, the base assembly also includes a switch assembly 122. The switch assembly 122 may include a push-button, toggle switch, or other form of binary or two-state switch electrically connected to the circuit 118. The primary purpose of the switch assembly 122 is to enable a user to manually activate the sanitizing operation. In some embodiments the switch assembly 122 also enables a user to manually terminate a sanitizing operation by interacting with the switch assembly 122 during a sanitizing operation. In some embodiments a processor in the circuit 118 is capable of detecting a long press or hold of the switch assembly by a user to enable a user to activate additional pre-programmed operations, such as enabling/disabling an automatic periodic sanitizing operation, the operation of one or more LED lights, the brightness of one or more LED lights, or changing the length of time required for a sanitizing operation.

In some embodiments, the bottle 100 does not include a switch assembly (e.g., a switch assembly is not required for proper function of the bottle). For example, periodic execution of the sanitizing operation may be triggered by a sensor that detects a condition (e.g., a threshold level of bacteria in the liquid, a threshold amount of liquid in the bottle 100, etc.) or a timer. Such embodiments may provide convenience to a user by maintaining a sanitized bottle interior without the need for any intervention by a user. In some embodiments, the bottle 100 does not include a switch and sensor for detecting bacteria. For example, periodic execution of the sanitizing operation may automatically occur in 1-12 hour increments (e.g., a sanitizing operation is automatically executed every hour or every two hours, etc.).

Figure 1B:
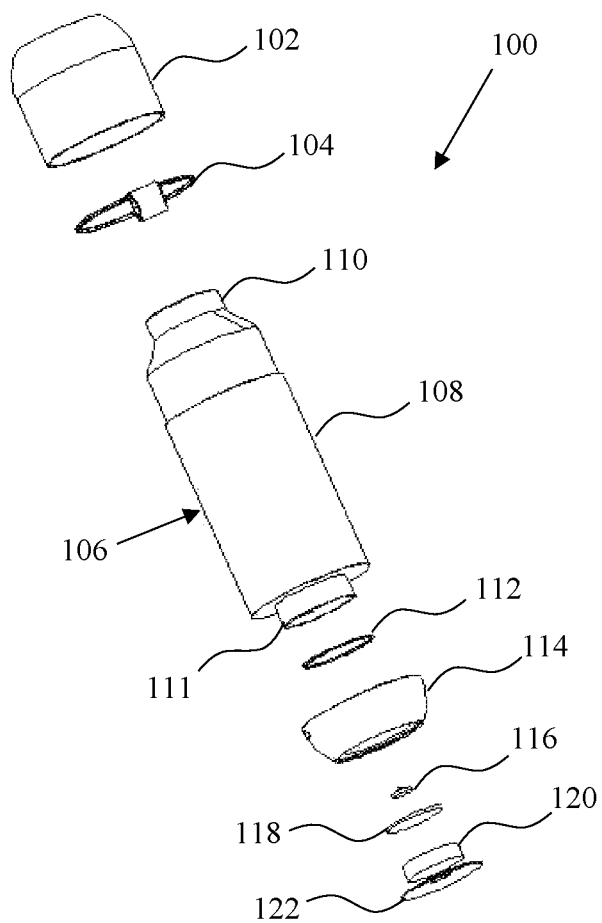
FIG. 1B shows an additional view of a self-sanitizing bottle, according to certain embodiments.

As shown in FIG. 1B, the storage body 106 may also form a lower opening 111 which interfaces with the sealing ring 112 and base cap 114 of the base assembly, according to certain embodiments. The lower opening 111 also provides a space into which the UV emitter 116 itself or a lens can be inserted so that light emitted from the UV emitter 116 is able to contact one or more interior surfaces (e.g., every interior surface) of the storage body 106 and cap 102, thereby contacting and sanitizing liquid (e.g., all liquid) stored in the bottle 100. The storage body 106 may be shaped in such a fashion that light from the UV emitter 116 shines directly on every surface. In some embodiments light from the UV emitter 116 does not shine directly on every surface but does shine on every surface by reflection off of interior surfaces of the storage body 106 and cap 102.

Figure 2:
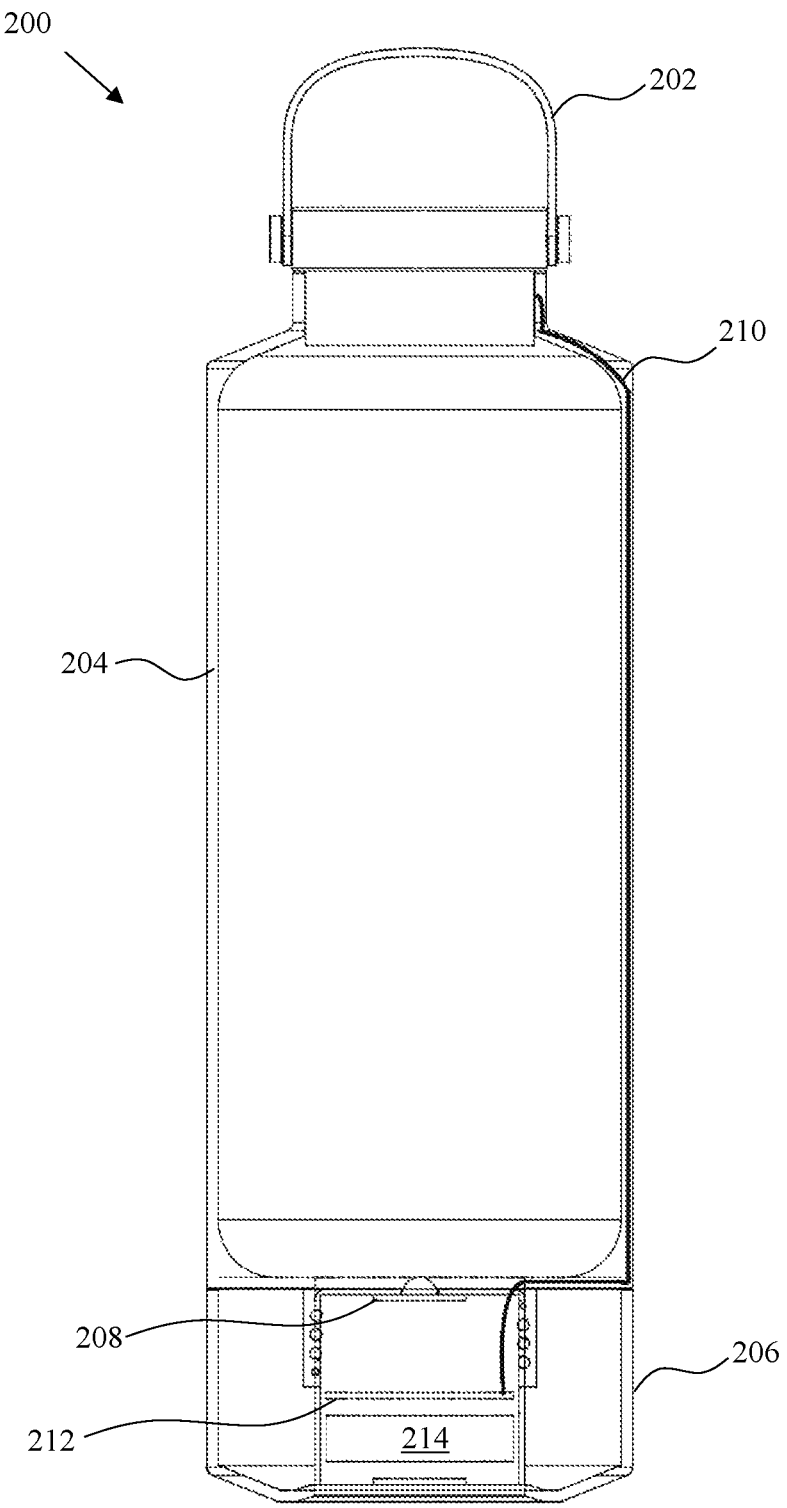
FIG. 2 shows a sectional view of a self-sanitizing bottle, according to certain embodiments.

Referring now to FIG. 2, an embodiment of a bottle 200 is shown which includes a cap 202, a storage body 204, a base assembly 206, a UV emitter 208, a circuit 212, a battery 214, and a cap wiring 210. In the depicted embodiment, the cap wiring 210 electrically connects cap 202 to circuit 212 when cap 202 is in a closed configuration secured to the bottle 200. The cap wiring 210 is configured to enable a processor in the circuit 212 to detect whether cap 202 is in a closed configuration or is detached from storage body 204. In some embodiments cap wiring 210 comprises a first wire and a second wire. The first wire carries an electrical signal from the processor to cap 202. The cap 202 includes electrical connections which conduct electrical current from the first wire into the second wire of the cap wiring 210 when the cap 202 is in a closed configuration. The processor in the circuit 212 may then detect when cap 202 is closed when an input detects an electrical signal from the second wire.

In some embodiments, cap wiring 210 may comprise one or more wires which instead carry power to one or more sensors in cap 202 and carry signals from the sensor back to a processor in the circuit 212. Sensors may include proximity sensors, switches or other sensors for detecting when the cap is in a closed configuration. The cap wiring 210 may be used to ensure that UV light is emitted from UV emitter 208 responsive to the bottle 200 being closed (e.g., only when the bottle 200 is closed). This increases user safety by ensuring that a user's eyes will not be struck by UV light from the UV emitter 208 because the processor is capable of deactivating the UV emitter 208 upon detecting that cap 202 is not closed or fully closed. Such a safety feature would override other programmed processor functions, including preset timers.

In some embodiments, after deactivating the UV emitter 208 responsive to detecting that cap 202 is not sufficiently closed, the processor may reactivate the UV emitter 208 responsive to detecting that the cap 202 is subsequently closed, thus allowing the sanitizing operation to continue after being interrupted when it is safe for a user.

In some embodiments, cap 202 includes electrically activated mechanisms which lock cap 202 in a closed configuration until a sanitizing operation is completed. In such embodiments the user's safety is similarly prioritized and the sanitizing operation will not have to be repeated if a user attempts to open cap 202 and inadvertently interrupts the sanitizing operation. Mechanisms for locking cap 202 in a closed position may include servos, latches, push-pull solenoids, or the like.

A method may be performed to sanitize a bottle (e.g., bottle 100 or 200). The method may be performed by processing logic that may include hardware (e.g., circuitry, dedicated logic, programmable logic, microcode, processing device, etc.), software (such as instructions run on a processing device, a general purpose computer system, or a dedicated machine), firmware, microcode, or a combination thereof. In one embodiment, the method may be performed, in part, by processor (e.g., of circuit 118 or 212) of the bottle. In some embodiments, a non-transitory storage medium stores instructions that when executed by a processor cause the processor to perform the method to sanitize a bottle.

For simplicity of explanation, the method to sanitize a bottle is depicted and described as a series of acts. However, acts in accordance with this disclosure can occur in various orders and/or concurrently and with other acts not presented and described herein. Furthermore, not all illustrated acts may be performed to implement the method in accordance with the disclosed subject matter. In addition, those skilled in the art will understand and appreciate that the method could alternatively be represented as a series of interrelated states via a state diagram or events. The method of sanitizing a bottle may include one or more of the following operations or acts by the processing logic.

The processing logic may receive an attached signal from a cap sensor of a sanitizing bottle (e.g., responsive to cap 102 being attached to storage body 106, etc.).

The processing logic may determine, based on the attached signal, that a cap of the sanitizing bottle is attached to a storage body of the sanitizing bottle.

In some embodiments, the processing logic may receive a first predetermined time delay signal from a timer of the sanitizing bottle responsive to a first predetermined time delay completing.

In some embodiments, the processing logic may receive user input via a switch of the sanitizing bottle responsive to a user engaging the switch.

Responsive to the determining that the cap is attached and receiving one or more of the first predetermined time delay signal or the user input, the processing logic may cause an ultraviolet (UV) emitter of the sanitizing bottle to emit UV light to one or more interior surfaces of the sanitizing bottle and may activate the timer.

In some embodiments, the processing logic may deactivate the UV emitter responsive to receiving one or more of a second predetermined time delay signal from the timer responsive to completion of a second predetermined time delay or a detached signal from the cap sensor responsive to the cap being detached from the storage body.

In some embodiments, subsequent to the deactivating of the UV emitter responsive to the receiving of the detached signal prior to the completion of the second predetermined time delay, the processing logic may receive a second attached signal from the cap sensor. The processing logic may determine, based on the second attached signal, that the cap is re-attached to the storage body. Responsive to determining that the cap is re-attached to the storage body, the processing logic may re-activate the UV emitter and the timer.

In alternate embodiments, it is contemplated that the bottle in present invention may be configured as any container requiring sanitation including, but not limited to, baby bottles, coolers, jugs, pitchers, Tupperware, re-usable plastic storage bags, water pouches, bladders, canteens, hydration packs, liquid dispenser, blender, teapot or lunchboxes. It is anticipated that the container may made from any material configured to store liquids or food products, wherein the material may be comprised of an insulated or non-insulated material that may be rigid or flexible in nature. The container may also comprise multiple compartments or multiple storage bodies within the container.

In one alternate embodiment, the present invention may comprise a container having a lid, a storage body having an outer surface and an inner surface, the storage body also having a first and second opening, a UV-light assembly removably or permanently secured to the storage body, at least one UV emitter located in the UV-light assembly, a circuit, a battery, and a lid wiring. The lid is configured to be removably attached to the first opening of the storage body. The UV-emitter is configured to emit light into the storage body and onto the interior surface through the second opening. In this contemplated embodiment, the lid wiring electrically connects the lid to the circuit when the lid is in a closed configuration secured to the container. The lid wiring is configured to enable a processor in the circuit to detect whether the lid is in a closed configuration or is detached from storage body. In some embodiments lid wiring comprises a first wire and a second wire. The first wire carries an electrical signal from the processor to the lid. The lid includes electrical connections which conduct electrical current from the first wire into the second wire of the lid wiring when the lid is in a closed configuration. The processor in the circuit may then detect when the lid is closed when an input detects an electrical signal from the second wire. In response to detecting a closed position of the lid the processor is configured to be able to activate the UV emitter. In response to detecting an open or detached position of the lid, the processor is configured to deactivate the UV emitter.

It is also anticipated that a method and system of detection of the position of the lid relative to the storage body may comprise an alternate embodiment wherein the wiring system as described herein may be configured as any sensor able to detect a closed or open position of the lid relative to the storage body. The sensor may be configured as a motion sensor, laser sensor, a touch sensor, or other.

In a further embodiment, the lid may further comprise a handle or other attachment configured for carrying or attachment to another body like a bag or backpack.

In further contemplated embodiment, the present invention may be configured without a lid or cap, wherein the storage container comprises at least one side wall which may be continuous, or at least two side walls, wherein the side wall or side walls are configured to seal a first opening of the storage container. In the embodiment of the continuous side wall, the side wall may be configured such that a first portion of the side wall is configured to removably seal to a second portion of the side wall, wherein when the first and second portions are sealed together, they constitute a closed position and wherein the first and second portions are detached they constitute an open position. In the embodiment of at least two side walls comprising at least a first and a second side wall, the first wall is configured to removably attach to or seal to the second side wall, wherein the first opening of the storage container is achieved by detaching the first side wall from the second side wall constituting an open position of the storage container. Similarly, the first opening of the storage container is achieved by detaching the first portion of the continuous side wall from the second portion of the continuous side wall.

It is contemplated that a method or system of detection of an open position or closed position of the first opening of the storage container may comprise a wiring system as described by FIG. 2. In alternate embodiment, the detection of an open position or closed position may comprise a system comprising any sensor configured to detect whether the first and second portions of the side wall are in a closed or open position or any sensor configured to detect whether the first and second side walls are in a closed or open position. The sensor may be an alternate wiring system, a motion sensor, a laser sensor or other sensor. The sensor may be integrated into at least one side wall of the storage container. This increases user safety by ensuring that a user's eyes will not be struck by UV light from the UV emitter because the processor is capable of deactivating the UV emitter upon detecting an open or partially open position of the storage container. Such a safety feature would override other programmed processor functions, including preset timers.

It is contemplated that the second opening of the container may be configured as a UV-light inlet. It is anticipated that the UV-light assembly and UV-light inlet may be positioned in any location in the storage body. In the preferred embodiment, the UV-light inlet is located in a bottom portion of the storage body. In a further embodiment, the container may further comprise a UV-light reflect configured to increase the intensity of UV-light and range of light exposure within the storage body.

It is also contemplated that the first opening of the container may be located in any portion of the storage body, including but not limited to, an upper or side portion of the storage body. The first opening may further comprise a spout, spicket or other attachment for liquid or solid entry or dispensing. A first opening attachment may also be configured as a filter.

What is claimed is:

1. A bottle for storing liquid, the bottle comprising:
   a removable cap;
   a storage body that defines a volume in which the liquid is to be stored, the storage body comprising a liquid inlet portion forming an upper opening, an ultraviolet (UV) light inlet portion forming a lower opening, and an interior surface, the liquid inlet portion being configured to be removably coupled to the cap;
   a cap sensor disposed on the storage body and configured to detect whether the cap is attached to the storage body;
   a base assembly affixed to the storage body, the base assembly comprising a base cap, a UV emitter configured to emit UV light having wavelengths from 100 nanometers (nm) to 290 nm, the base assembly being affixed to the UV light inlet portion of the storage body to emit light via the UV emitter into the interior surface of the storage body; and
   a processor coupled to the cap sensor and the UV emitter, wherein the base cap includes a transparent lens arranged at the lower opening of the storage body such that the lens is between the volume of the storage body and the UV emitter such that the lens contacts the liquid stored in the storage body, and the lens is configured within the base cap to form a water-tight seal that prevents liquid stored in the storage body from contacting the UV emitter, and
   wherein the processor is configured to perform a sanitizing operation by activating the UV emitter responsive to determining the cap is both attached to the storage body and arranged in a fully closed configuration to the storage body, and the processor is configured to deactivate the UV emitter responsive to determining the cap is not attached to the storage body and responsive to determining the cap is not in a fully closed configuration to the storage body,
   wherein the bottle further comprises a locking mechanism that locks the cap in a closed configuration to the storage body until the sanitizing operation is completed,
   wherein the bottle further comprises a battery, a timer, and a switch, wherein the processor is coupled to the battery, the timer, and the switch, wherein the battery is configured to provide power to the processor, wherein the processor is configured to provide power to the UV emitter, the switch, the cap sensor, and the timer, and
   wherein the processor is configured to execute the sanitizing operation responsive to receiving user input via the switch, the sanitizing operation comprising:
      locking of the locking mechanism that locks the cap in the closed configuration of the storage body;
      activating the UV emitter to emit UV light towards the interior surface of the storage body;
      activating the timer;
      deactivating the UV emitter responsive to one or more of determining, based on the timer, completion of a predetermined time delay or determining, via the cap sensor, the cap is not attached to the storage body; and
      unlocking of the locking mechanism upon completion of the sanitizing operation.

2. The bottle of claim 1, wherein the cap sensor comprises one or more wires electrically connecting the processor to the cap responsive to the cap being attached to the storage body, wherein the one or more wires extend from the base assembly, through the storage body, and to the liquid inlet portion of the storage body.

3. The bottle of claim 1 further comprising one or more LEDs controlled by the processor, and wherein the sanitizing operation further comprises changing a power state of at least one of the one or more LEDs.

4. The bottle of claim 3, wherein the bottle further comprises a charging port configured to receive a charging cable to recharge the battery.

5. The bottle of claim 3, wherein the bottle further comprises an inductive charging portion configured to recharge the battery responsive to being placed proximate a corresponding inductive charging pad.

6. The bottle of claim 1, wherein the predetermined time delay comprises a delay of between 30 and 90 seconds.

7. The bottle of claim 1, wherein the sanitizing operation further comprises:
   subsequent to the deactivating of the UV emitter responsive to the determining that the cap is not attached to the storage body prior to the completion of the predetermined time delay, determining that the cap is attached to the storage body; and responsive to the determining that the cap is attached to the storage body, reactivating the UV emitter and the timer.

8. The bottle of claim 1, wherein the liquid inlet portion of the storage body further comprises a first threaded surface and the cap further comprises a second threaded surface, the first threaded surface and second threaded surface configured to interact with one another to enable the cap to be selectively attached to or detached from the storage body.

9. The bottle of claim 8, wherein the base assembly further comprises a seal configured to prevent passage of liquid stored in the storage body into the base cap.

10. The bottle of claim 9, wherein the UV light inlet portion of the storage body further comprises a third threaded surface and the base cap of the base assembly further comprises a fourth threaded surface, the third threaded surface and second threaded surface configured to interact with one another to enable the base assembly to be selectively attached to or detached from the storage body.

11. The bottle of claim 1, wherein the interior surface of the storage body comprises a material selected from the group consisting of coated aluminum, uncoated aluminum, coated steel, uncoated steel, and glass.

12. A reusable sanitizing bottle comprising:
a storage body that defines a volume in which a liquid is to be stored, the storage body comprising an ultraviolet (UV) light inlet portion forming an opening;
a cap configured to removably attach to the storage body;
a cap sensor disposed on the storage body to determine whether the cap is attached to the storage body;
a UV emitter to emit UV light in the storage body;
a transparent lens arranged between the volume of the storage body at the ultraviolet (UV) light inlet portion and the UV emitter such that the lens contacts the liquid stored in the storage body, and the lens forms a water-tight seal that prevents liquid stored in the storage body from contacting the UV emitter; and
a processor coupled to the cap sensor and the UV emitter, wherein the processor is configured to perform a sanitizing operation by activating the UV emitter responsive to determining, via the cap sensor, the cap is both attached to the storage body and arranged in a fully closed configuration to the storage body, and the processor is to deactivate the UV emitter responsive to determining, via the cap sensor, the cap is not attached to the storage body and responsive to determining the cap is not in a fully closed configuration to the storage body,
wherein the bottle further comprises a locking mechanism that locks the cap in a closed configuration to the storage body until the sanitizing operation is completed,
wherein the bottle further comprises a battery, a timer, and a switch, wherein the processor is coupled to the battery, the timer, and the switch, wherein the battery is configured to provide power to the processor, wherein the processor is configured to provide power to the UV emitter, the switch, the cap sensor, and the timer, and
wherein the processor is configured to execute the sanitizing operation responsive to receiving user input via the switch, the sanitizing operation comprising:
locking of the locking mechanism that locks the cap in the closed configuration of the storage body;
activating the UV emitter to emit UV light towards the interior surface of the storage body;
activating the timer;
deactivating the UV emitter responsive to one or more of determining, based on the timer, completion of a predetermined time delay or determining, via the cap sensor, the cap is not attached to the storage body; and
unlocking of the locking mechanism upon completion of the sanitizing operation.

13. The sanitizing bottle of claim 12, wherein the processor is to activate the UV emitter further responsive to determining, via the timer, completion of another predetermined time delay.

14. A method comprising:
providing a sanitizing bottle that includes
a storage body that defines a volume in which a liquid is to be stored, the storage body comprising an ultraviolet (UV) light inlet portion forming an opening,
a cap configured to removably attach to the storage body,
a cap sensor disposed on the storage body to determine whether the cap is attached to the storage body,
a UV emitter to emit UV light in the storage body,
a transparent lens arranged between the volume of the storage body at the ultraviolet (UV) light inlet portion and the UV emitter such that the lens contacts the liquid stored in the storage body, and the lens forms a water-tight seal that prevents liquid stored in the storage body from contacting the UV emitter, and
a processor;
responsive to receiving an attached signal from the cap sensor of the sanitizing bottle,
determining, by the processor, based on the attached signal, that the cap is both attached to the storage body and arranged in a fully closed configuration to the storage body;
receiving, by the processor, one or more of a first predetermined time delay signal from a timer of the sanitizing bottle responsive to a first predetermined time delay completing or user input via a switch of the sanitizing bottle responsive to a user engaging the switch;
responsive to the determining that the cap is both attached and arranged in a fully closed configuration to the storage body, locking, by the processor, the cap to the storage body in the fully closed configuration;
further responsive to the determining that the cap is both attached and arranged in the fully closed configuration to the storage body and receiving the one or more of the first predetermined time delay signal or the user input, performing a sanitizing operation by causing the ultraviolet (UV) emitter of the sanitizing bottle to emit UV light to one or more interior surfaces of the sanitizing bottle and activating the timer, wherein the cap is maintained locked in the fully closed configuration until the sanitizing operation is completed; and
unlocking, by the processor, the cap from the closed configuration upon completion of the sanitizing operation.

15. The method of claim 14 further comprising:
deactivating, by the processor, the UV emitter responsive to receiving one or more of:
a second predetermined time delay signal from the timer responsive to completion of a second predetermined time delay; or
a detached signal from the cap sensor responsive to the cap being detached from the storage body.

16. The method of claim 15 further comprising:
subsequent to the deactivating of the UV emitter responsive to the receiving of the detached signal prior to the completion of the second predetermined time delay, receiving a second attached signal from the cap sensor;

determining, based on the second attached signal, that the cap is re-attached to the storage body; and responsive to the determining that the cap is re-attached to the storage body, re-activating the UV emitter and the timer.

17. A self-sanitizing container comprising:

a storage body that defines a volume in which a liquid is to be stored, the storage body comprising:
   a first opening;
   an ultraviolet (UV) light inlet portion; and
   an interior surface;
      the first opening being configured to exist in a closed position or an open position at least one sensor configured to detect whether the first opening is in a closed position or an open position; and at least one UV-light assembly comprising:
   a main body;
   at least one UV emitter located in the main body and configured to emit UV light having wavelengths from 100 nanometers (nm) to 290 nm;
   a processor coupled to the sensor and UV emitter;

wherein the container further comprise a transparent lens arranged at a second opening of the storage body such that the lens is between the volume of the storage body and the at least one UV emitter such that the lens contacts the liquid stored in the storage body, and the lens is configured within the main body to form a water-tight seal that prevents liquid stored in the storage body from contacting the at least one UV emitter;

wherein the UV-light assembly is configured to removably attach to the UV light inlet portion of the storage body and is configured to emit light via the UV emitter onto the interior surface of the storage body; and wherein the processor is configured to perform a sanitizing operation by activating the UV emitter responsive to determining a cap is both attached to the first opening of the storage body and the cap is in a fully closed position relative to the storage body, and the processor is configured to deactivate the UV emitter responsive to determining the cap is not in a fully closed position of the first opening wherein the container further comprises a locking mechanism that locks the cap in a closed configuration to the storage body until the sanitizing operation is completed, wherein the container further comprises a battery, a timer, and a switch, wherein the processor is coupled to the battery, the timer, and the switch, wherein the battery is configured to provide power to the processor, wherein the processor is configured to provide power to the UV emitter, the switch, the cap sensor, and the timer, and wherein the processor is configured to execute the sanitizing operation responsive to receiving user input via the switch, the sanitizing operation comprising:
   locking of the locking mechanism that locks the cap in the closed configuration of the storage body;
   activating the UV emitter to emit UV light towards the interior surface of the storage body;
   activating the timer;
   deactivating the UV emitter responsive to one or more of determining, based on the timer, completion of a predetermined time delay or determining, via the cap sensor, the cap is not attached to the storage body; and
   unlocking of the locking mechanism upon completion of the sanitizing operation.

\* \* \* \* \*